US012151090B2

(12) United States Patent
Ganapathy (10) Patent No.: US 12,151,090 B2
(45) Date of Patent: Nov. 26, 2024

(54) PASSIVE SAFETY DEVICE, INJECTION DEVICE COMPRISING THE SAME, AND METHOD FOR MANUFACTURING SAID INJECTION DEVICE

(71) Applicant: Becton Dickinson Holdings Pte. Ltd., Singapore (SG)

(72) Inventor: Manicavasagam Ganapathy, Hosur (IN)

(73) Assignee: Becton Dickinson Holdings Pte. Ltd., Singapore (SG)

( * ) Notice: Subject to any disclaimer, the term of this patent is extended or adjusted under 35 U.S.C. 154(b) by 60 days.

(21) Appl. No.: 17/761,013

(22) PCT Filed: Sep. 16, 2020

(86) PCT No.: PCT/SG2020/050529
§ 371 (c)(1),
(2) Date: Mar. 16, 2022

(87) PCT Pub. No.: WO2021/054895
PCT Pub. Date: Mar. 25, 2021

(65) Prior Publication Data
US 2022/0339368 A1 Oct. 27, 2022

(30) Foreign Application Priority Data

Sep. 17, 2019 (EP) ..................................... 19197826

(51) Int. Cl.
*A61M 5/32* (2006.01)
(52) U.S. Cl.
CPC .......... *A61M 5/3245* (2013.01); *A61M 5/326* (2013.01); *A61M 5/3293* (2013.01); *A61M 2005/3247* (2013.01); *A61M 2207/00* (2013.01)

(58) Field of Classification Search
CPC .. A61M 5/3245; A61M 5/326; A61M 5/3293; A61M 5/3247; A61M 5/3271;
(Continued)

(56) References Cited

U.S. PATENT DOCUMENTS

| | | |
|---|---|---|
| 4,842,587 A | 6/1989 | Poncy |
| 4,894,055 A | 1/1990 | Sudnak |

(Continued)

FOREIGN PATENT DOCUMENTS

| | | |
|---|---|---|
| EP | 2578257 A1 | 4/2013 |
| KR | 1020180084008 A | 7/2018 |

(Continued)

*Primary Examiner* — Laura A Bouchelle
*Assistant Examiner* — Sarah Dympna Grasmeder
(74) *Attorney, Agent, or Firm* — The Webb Law Firm (57) ABSTRACT

The passive safety device comprises a sleeve having a proximal end configured to be secured to a distal tip of the injection device, a hub slidably mounted onto the sleeve between a pre-use position, an injection position wherein the hub is proximally located with regard to the pre-use position, and a safety position wherein the hub is distally located with regard to the injection position, a biasing element configured to urge the hub distally towards the safety position, and a protector configured to slide together with the hub relative to the sleeve between the pre-use position and the injection position. The safety device may be configured to block a distal movement of the protector when the hub is in the injection position so that the protector is prevented from sliding back together with the hub in a distal direction.

17 Claims, 6 Drawing Sheets

(58) Field of Classification Search
CPC .............. A61M 5/3243; A61M 5/3232; A61M 2005/3267; A61M 2005/3247
See application file for complete search history.

(56) References Cited

U.S. PATENT DOCUMENTS

| | | | |
|---|---|---|---|
| 5,250,037 A | | 10/1993 | Bitdinger |
| 6,391,003 B1 | * | 5/2002 | Lesch, Jr. .............. A61M 5/326 |
| | | | 604/110 |
| 9,694,141 B2 | | 7/2017 | Slemmen et al. |
| 10,159,805 B2 | | 12/2018 | Schoonmaker |
| 10,213,561 B2 | | 2/2019 | Liversidge |
| 10,888,670 B2 | | 1/2021 | McElroy et al. |
| 2004/0127857 A1 | | 7/2004 | Shemesh et al. |
| 2009/0312705 A1 | | 12/2009 | Grunhut et al. |
| 2009/0326477 A1 | | 12/2009 | Liversidge |
| 2010/0137810 A1 | * | 6/2010 | Chandrasekaran ... A61M 5/326 |
| | | | 604/198 |
| 2010/0249821 A1 | * | 9/2010 | Karbowniczek ... A61B 5/15117 |
| | | | 606/181 |
| 2011/0092914 A1 | | 4/2011 | Clayson |
| 2014/0039407 A1 | | 2/2014 | Schoonmaker |
| 2014/0039408 A1 | | 2/2014 | Perot et al. |
| 2015/0032061 A1 | * | 1/2015 | Jakob ................. A61M 5/3245 |
| | | | 604/198 |
| 2020/0222637 A1 | * | 7/2020 | Carrel ................. A61M 5/3216 |

FOREIGN PATENT DOCUMENTS

| | | |
|---|---|---|
| WO | 2007129324 A2 | 11/2007 |
| WO | 2009126720 A1 | 10/2009 |
| WO | 2011098831 A1 | 8/2011 |
| WO | 2013192328 A1 | 12/2013 |
| WO | 2019033092 A1 | 2/2019 |

* cited by examiner

PASSIVE SAFETY DEVICE, INJECTION DEVICE COMPRISING THE SAME, AND METHOD FOR MANUFACTURING SAID INJECTION DEVICE

CROSS-REFERENCE TO RELATED APPLICATIONS

This application is the United States national phase of International Application No. PCT/SG2020/050529 filed Sep. 16, 2020, and claims priority to European Patent Application No. 19197826.1 filed Sep. 17, 2019, the disclosures of which are hereby incorporated by reference in their entirety.

BACKGROUND OF THE INVENTION

Field of the Invention

The present disclosure relates to a passive needle safety device, an injection device, such as a prefilled syringe, comprising this passive needle safety device, and a method for manufacturing said injection device.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to the passive safety device or injection device of the invention, and the "proximal direction" is to be understood as meaning the opposite direction to said direction of injection, that is to say the direction towards the user's hand.

Injection devices, such as pre-fillable or prefilled syringes, usually comprise a hollow body or barrel forming a container for a medical product. This body comprises a distal end in the form of a longitudinal tip defining an axial passageway through which the medical product is expelled from the container. The distal end is equipped with a needle that is designed to be inserted into the skin of a patient and through which the product to be injected passes to an injection site.

In order to minimize the risks of needle stick injuries, it is known to furnish the injection devices with a safety device that protects the needle after an injection. This safety device usually comprises a sleeve that slides relative to the distal end of the injection device and covers the needle after the withdrawal of the needle from the injection site.

The safety devices may be either active or passive. The active safety devices need to be activated by the user, i.e. they require the user to undertake a specific action so as to trigger the protection of the needle once the injection is completed. In contrast, the passive safety devices do not need a user to perform any action to ensure that the needle is protected once the injection is completed.

Description of Related Art

Document WO2011098831 discloses such a passive safety device. This safety device comprises a sleeve which is axially slidable between a needle protecting position and a non-protecting position. The proximal part of this sleeve is configured to deform radially outwardly so as to reach the non-protecting position. This deformation enables to store energy so that the proximal part of said sleeve acts as a spring urging the whole sleeve back to its initial protecting position once the needle is removed from the injection site.

However, in order to achieve an effective spring effect, the proximal part of the sleeve needs to be deformed at its greatest extent. This involves that the needle to be inserted a quite long distance into the injection site. This may be stressful or harmful for a user. Besides, as noted above, the proximal part of the sleeve is configured to extend radially outward. This outward deformation renders the safety device quite radially cumbersome. Moreover, deformation of the sleeve is visible and may worry a user.

The documents U.S. Pat. No. 4,894,055 and WO2013192328 disclose needle guards.

There is therefore a need for a more compact and easier to manufacture passive safety device, said safety device allowing a reliable protection of the needle once the injection is completed.

SUMMARY OF THE INVENTION

An aspect of the invention is a passive safety device comprising:
- a sleeve having a proximal end configured to be secured to a distal tip of the injection device;
- a hub slidably mounted onto the sleeve between a pre-use position, an injection position wherein the hub is proximally located with regard to the pre-use position, and a safety position wherein the hub is distally located with regard to the injection position,
- a biasing element configured to urge the hub distally towards the safety position, and
- a protector configured to slide together with the hub relative to the sleeve between the pre-use position and the injection position, the safety device further comprising
- first blocking means configured to block a distal movement of the protector when the hub is in the injection position so that the protector is prevented from sliding back together with the hub in a distal direction, and
- second blocking means configured to block a proximal movement of the hub when the hub is in the safety position.

The needle safety device of the invention thus permits a reliable protection of the needle after an injection while being compact and easy to manufacture.

In this application, by "passive safety device" it is meant a needle safety device which does not require the user to undertake any action after injection so as to make the needle be protected after removal of the needle from an injection site.

In an embodiment, the first blocking means are first snapping means configured to make the protector be snapped with the sleeve when the hub reaches the injection position.

This provides a compact and easy to manufacture safety device.

In an embodiment, the first snapping means are provided on the protector.

This feature improves the compactness of the safety device.

In an embodiment, the first snapping means comprise at least one first resilient leg that is slidably engaged in a longitudinal slot of the sleeve when the hub moves from the pre-use position towards the injection position, said at least one first resilient leg being configured to radially deform against a distal side of a blocking member of the sleeve and abut a proximal side of said blocking member when the hub is in the injection position.

This provides a compact and easy to manufacture solution in order to block any distal movement of the protector when the hub is in the injection position.

In an embodiment, the second blocking means are second snapping means configured to make the hub be snapped when the hub reaches said safety position.

This provides a compact and easy to manufacture safety device.

In an embodiment, the second snapping means are provided on the protector.

This feature improves the compactness of the safety device.

In an embodiment, the second snapping means comprise at least one second resilient leg that is slidably engaged in a proximal slot of the hub when the hub moves from the injection position towards the safety position, said at least one resilient leg being configured to radially deform against a distal side of a blocking member of the hub and abut a proximal side of said blocking member when the hub is in the safety position.

This provides a compact and easy to manufacture solution in order to block any proximal movement of the hub once the hub reaches the safety position.

In an embodiment, the hub comprises a proximal pushing surface that defines a proximal end of the proximal slot of the hub, said proximal pushing surface being configured to abut against the at least one second resilient leg in order to cause said protector to slide together with the hub when the hub moves from the pre-use position to the injection position.

This improves the compactness of the safety device.

In an embodiment, the second snapping means comprise at least one longitudinal leg of the sleeve that is slidably engaged in a distal slot of the hub when the hub moves from the injection position towards the safety position, said at least one longitudinal leg being configured to radially deform against a distal side of a retaining member of the hub and to abut against a proximal side of said retaining member when the hub is in the safety position.

The longitudinal leg of the sleeve may comprise a radial protrusion that is configured to abut against a distal side of the retaining member of the hub in the pre-use position so as to retain the hub in this pre-use position against the action of the biasing element.

In an embodiment, the hub comprises at least one inner retaining element, such as a retaining hook, the biasing element comprises a distal end abutting against said inner retaining element in order to exert a distal force on the hub, and the sleeve has a longitudinal slot provided with an open distal end in order to allow said at least one retaining element to penetrate and slide into said longitudinal slot when the hub moves towards the injection position.

This improves the compactness of the safety device.

In an embodiment, the protector comprises a support ring, the first blocking means comprising at least one first resilient leg proximally extending from said support ring and the second blocking means comprising at least one second resilient leg distally extending from said support ring.

As a result, the first resilient legs and the second resilient legs are located at opposite sides of the support ring. This improves the compactness of the safety device.

In an embodiment, the at least one first resilient leg and the at least one second resilient leg are offset in a circumferential direction of the support ring.

As a result, the first resilient legs and the second resilient legs alternate along the support ring. This improves the compactness of the safety device.

In an embodiment, the protector is made of two parts configured to be assembled to each other directly on the hub.

This makes the safety device easier to manufacture. Each of the two parts that form the protector may correspond to a semi-circular half of said support ring. The two parts may be identical.

Another aspect of the invention is an injection device comprising the above-described passive safety device.

Another aspect of the invention is a method for manufacturing the above-described injection device, comprising the steps of:
 (i) securing the needle of the passive needle safety device onto a distal tip of the injection device;
 (ii) positioning the biasing element of the passive needle safety device into the sleeve;
 (iii) positioning the hub of the passive needle safety device onto the sleeve against the action of the biasing element;
 (iv) positioning the protector of the passive needle safety device onto the hub and the sleeve.

BRIEF DESCRIPTION OF THE DRAWINGS

The invention and the advantages arising therefrom will clearly emerge from the detailed description that is given below with reference to the appended drawings as follows.

DETAILED DESCRIPTION

Figure 1:
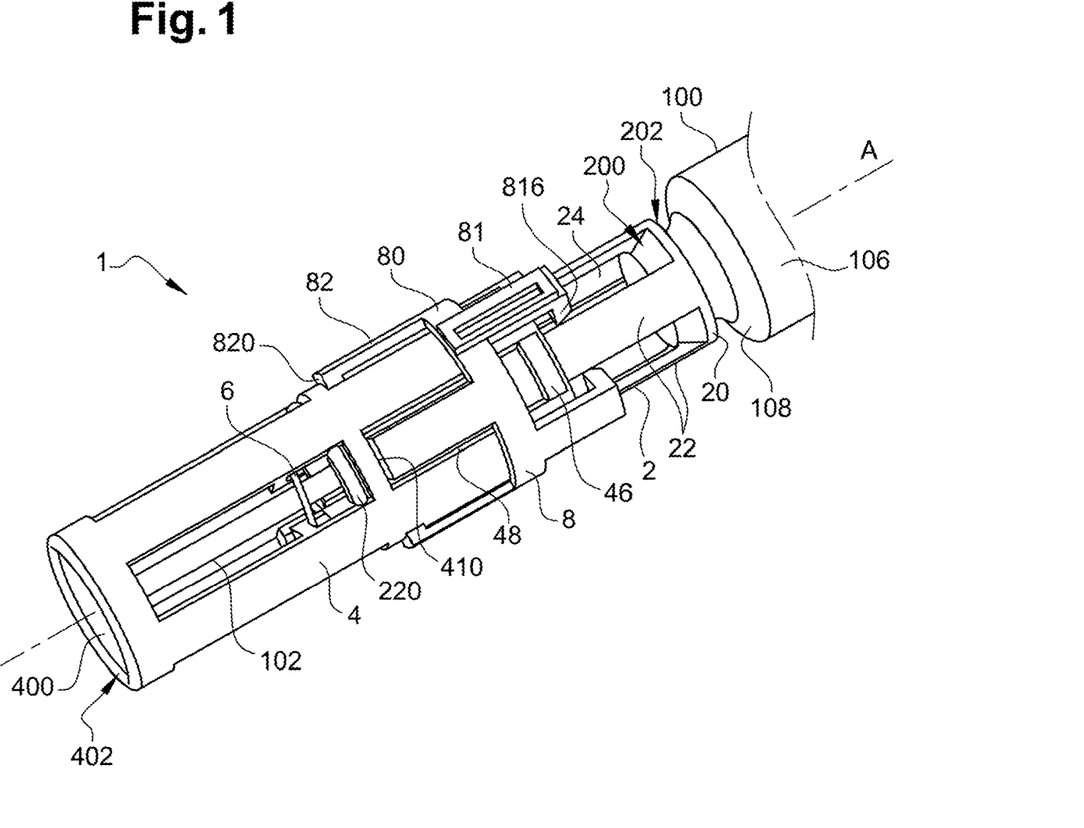
FIG. 1 is a perspective view of a safety device according to an embodiment of the invention.

With reference to FIG. 1 is shown a passive safety device 1 according to an embodiment of the invention. The passive safety device 1 is configured to cover the needle 102 of an injection device 100 at the end of an injection, in order to prevent needle stick injuries.

Figure 8:
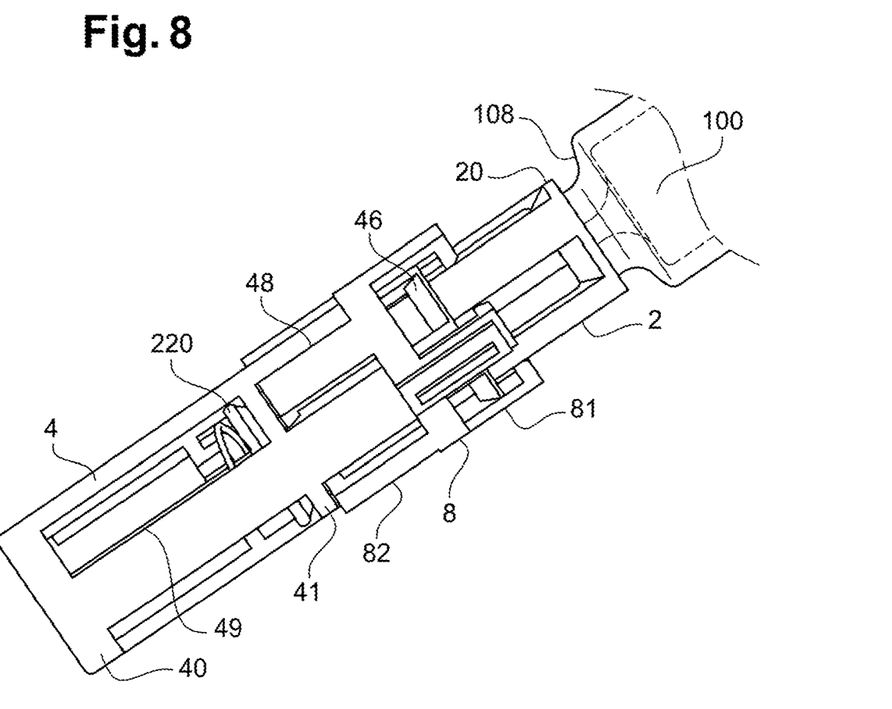
FIG. 8 is a perspective view of a safety device according to an embodiment of the invention, in the pre-use position.

The safety device 1 may adopt three successive positions: a pre-use position (FIGS. 1, 8, 11) wherein the safety device 1 is ready to perform an injection, an injection position (FIGS. 9, 12) wherein the safety device 1 uncovers the needle to allow the needle 102 to enter an injection site, and a safety position (FIG. 10, 13) wherein the safety device 1 covers the needle 102 to prevent needle stick injuries. The pre-use position and the safety position may be identical or different.

With reference to FIGS. 1, 2, 3A and 3B, the safety device 1 comprises a sleeve 2 that is configured to be fixedly attached onto a distal tip 104 of the injection device 100, a hub 4 that is slidably mounted on the sleeve 2, a biasing element 6 urging the hub 4 in a distal direction, and a protector 8 that is slidably mounted onto the sleeve 2. The safety device 1 further comprises first blocking means configured to block the protector 8 when the hub 4 reaches the injection position, and second blocking means configured to block the hub 4 when the hub 4 is in the safety position, as will be described in further details below.

The tubular sleeve 2 longitudinally extends along a longitudinal axis A. The sleeve 2 is configured to surround the distal tip 104 and a proximal part of the needle 102. The sleeve 2 comprises a proximal end and an opposite distal end. The proximal end is configured to be secured onto the distal tip 104 of the injection device 100, for example by gluing, screwing, interlocking, press-fitting, etc. The sleeve 2 comprises a blocking member, that may be located at the proximal end of the sleeve 2 and that may be in the form of a securing ring 20. As visible on FIG. 3A, the securing ring 20 defines a central through-opening 204 that accommodates the distal tip 104. The securing ring 20 also has a proximal side and an opposite distal side. The distal side may define a slanted surface 200. The proximal side may define an abutment surface 202.

Figure 3A:
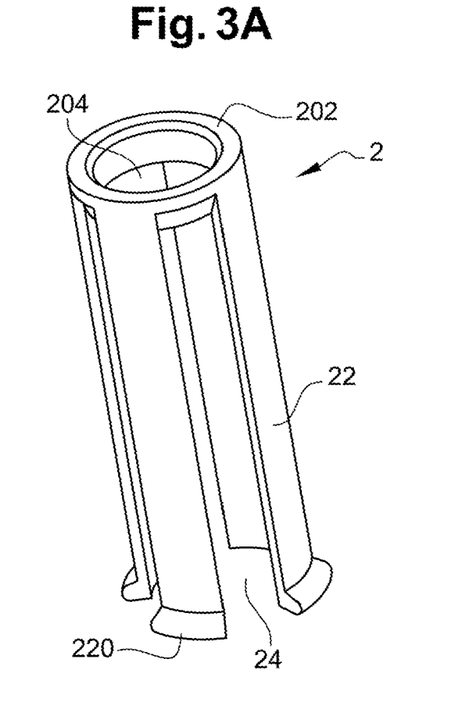
FIG. 3A is a perspective view of the sleeve of a safety device according to an embodiment of the invention.
Figure 3B:
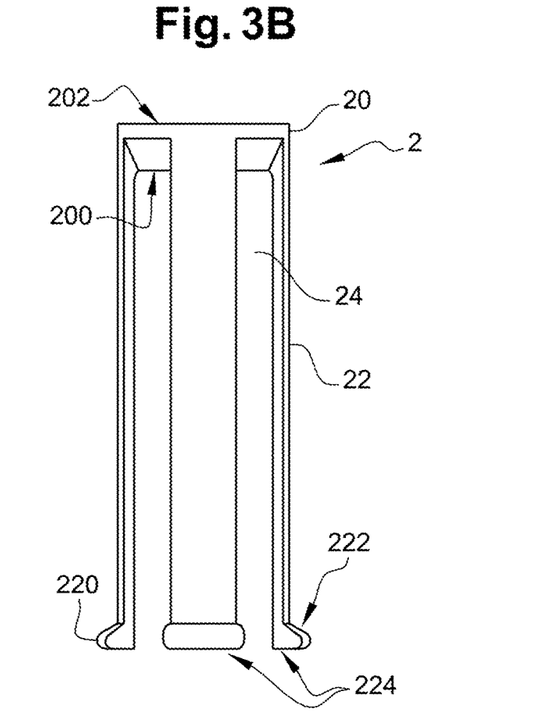
FIG. 3B is a side view of the sleeve of a safety device according to an embodiment of the invention.

The sleeve 2 may further include one or several longitudinal legs 22 that are separated from each other by longitudinal slots 24. The longitudinal legs 22 and the longitudinal slots 24 may extend parallel to the longitudinal axis A. The longitudinal slots 24 may be opened at their distal end and closed by the securing ring 20 at their proximal end. The longitudinal legs 22 may have a free distal end that may form the distal end of the sleeve 2, and an opposite proximal end that may be connected to the securing ring 20. The longitudinal legs 22 thus distally extend from said securing ring 20. The longitudinal legs 22 may be regularly distributed along the securing ring 20. The longitudinal legs 22 of the sleeve 2 may be configured to deflect radially inwardly. The longitudinal legs 22 may comprise a radial protrusion 220, such as an outwardly extending radial protrusion 220, whose function will appear hereinafter. This radial protrusion 220 may be located at the free distal end of the longitudinal legs 22. The radial protrusion 220 has a proximal side, that may define a possibly slanted, deflecting and/or retaining surface 222, and a distal side, that may define a blocking surface 224.

Figure 2:
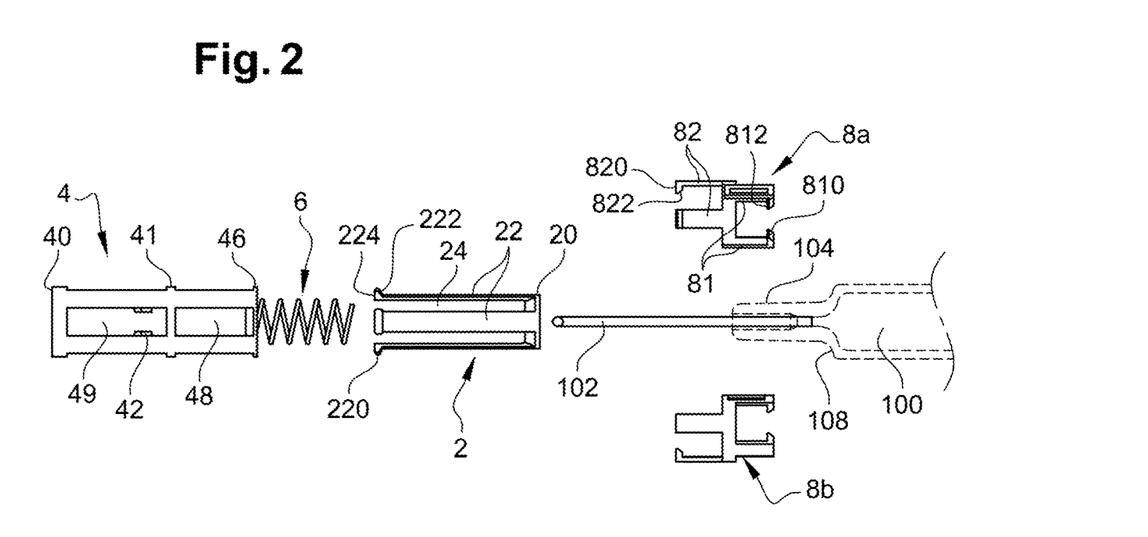
FIG. 2 is an exploded view of a safety device according to an embodiment of the invention.
Figure 4:
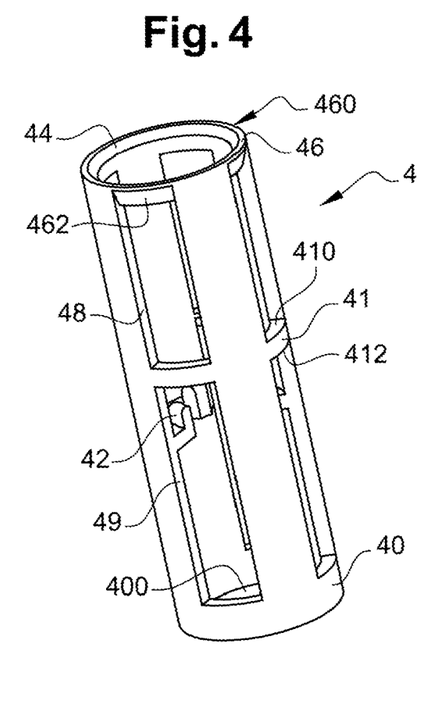
FIG. 4 is a perspective view of the hub of a safety device according to an embodiment of the invention.

With reference to FIGS. 1, 2 and 4, the hub 4 longitudinally extends along the longitudinal axis A. The hub 4 surrounds the sleeve 2. More specifically, the hub 4 is slidably mounted onto the sleeve 2 along the axis A between the pre-use position (FIGS. 1, 8, 11) wherein a distal end of the hub 4 may be configured to be distally located beyond a tip of the needle 102 so as to cover the needle 102, the injection position (FIGS. 9, 12) wherein the hub 4 is proximally retracted relative to the pre-use position so that the hub 4 uncovers the needle 102, and the safety position (FIGS. 10, 13) wherein the distal end of the hub 4 is configured to distally extend beyond the tip of the needle 102, so that the hub 4 covers the needle 102 back in order to avoid needle stick injuries.

The tubular hub 4 has a distal end and an opposite proximal end. The distal end defines a central opening 400 that is configured to let the needle 102 extend through said opening 40 in order to perform the injection. The distal end of the hub 4 further comprises an abutment surface 402 configured to contact the injection site, such as typically the skin of a patient, and to push the hub 4 proximally towards the injection position as the needle 102 enters the injection site. The abutment surface 402 may encircle the opening 400. As shown on FIG. 4, the proximal end of the hub 4 defines an opening 44 that receives the sleeve 2.

The hub 4 comprises a blocking member that may be located at the proximal end of the hub 4. The blocking member may be in the form of a blocking ring 46. Said blocking ring 46 has a proximal side and an opposite distal side. As best shown on FIG. 4, the proximal side defines a blocking surface 460. The distal side may define a slanted deflecting surface 462.

The hub 4 comprises one or several proximal slots 48 extending parallel to the longitudinal axis A. The proximal slots 48 may extend above and be aligned with the longitudinal legs 22 of the sleeve 2. The proximal slots 48 are closed at their proximal end by the blocking ring 46. The proximal slots 48 may also be closed at their distal end by a pushing surface 410, said pushing surface 410 being configured to push the protector 8 in the proximal direction when the hub 4 moves towards the injection position, so that the protector 8 slides together with the hub 4 towards the injection position.

The hub 4 may comprise one or several distal slots 49 that extend parallel to the longitudinal axis A. The distal slots 49 are aligned with the proximal slots 48 and are located distally relative to the proximal slots 48. The distal slots 49 may be closed at their distal end by a distal ring 40 that may form the distal end of the hub 4 and thus delimits the central opening 400 and the abutment surface 402. The distal slots 49 may be closed at their proximal end by a distal retaining surface 412. The distal retaining surface 412 may be configured to abut against the radial protrusions 220 of the longitudinal legs 22 so as to maintain the hub 4 in the pre-use position against the force exerted by the biasing element 6, prior to an injection. The proximal and/or distal slots 48, 49 may be regularly distributed along a circumferential direction of the hub 4.

The radial protrusions 220 of the sleeve 2 and the distal slots 49 of the hub 4 may also act as guiding means so as to guide the translation of the hub 4 relative to the sleeve 2.

The hub 4 may comprise a retaining member that may be located at the distal end of the proximal slots 48 and/or at the proximal end of the distal slots 49. The retaining member may be in form of an intermediate ring 41 that may separate the proximal slots 48 from the adjacent distal slots 49. The intermediate ring 41 comprises a proximal side that may define the pushing surface 410. The intermediate ring 41 comprises a distal side that may define the distal retaining surface 412. Said distal retaining surface 412 may be slanted to favor an inward deformation of the longitudinal legs 22 of the sleeve 2 when said distal retaining surface 412 abuts against the radial protrusions 220. Therefore, the radial protrusions 220 may disengage the distal slots 49 and engage the proximal slots 48 when the hub 4 is moved towards the safety position.

The hub 4 may comprise one or several retaining elements, such as hooks 42, that may extend from an inner lateral wall of the hub 4 so as to provide a support for a distal end of the biasing element 6. These retaining elements are configured to enter and slide along the longitudinal slots 24 of the sleeve 2 when the hub 4 moves towards the injection position, so that the biasing element 6 stores energy.

The biasing element 6 may be a spring whose distal end is connected to the hub 4, for example by means of the inwardly protruding hooks 42, and whose proximal end is secured in-between the sleeve 2 and the distal tip 104.

Figure 5:
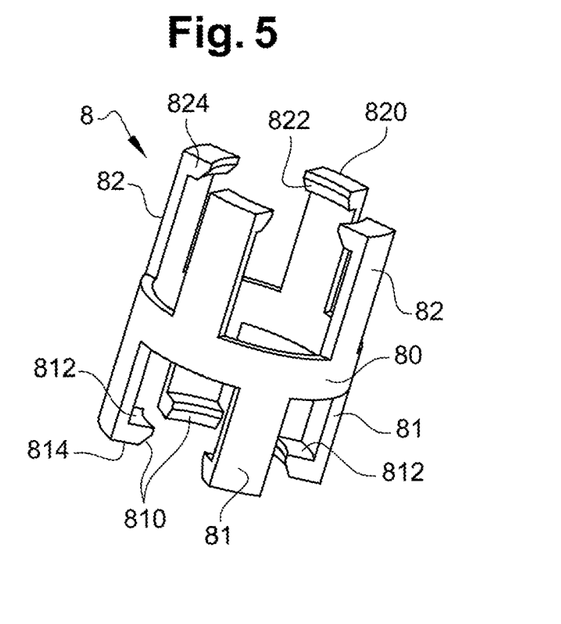
FIG. 5 is a perspective view of a protector of a safety device according to an embodiment of the invention.

With reference to FIGS. 1, 2 and 5, the protector 8 surrounds the sleeve 2 and is proximally located relative to the hub 4. The protector 8 is configured to slide together with the hub 4 onto the sleeve 2 when the hub 4 moves from the pre-use position to the injection position. The protector 8 thus comprises a distal abutment surface 820, said distal abutment surface 820 being configured to be pushed by a pushing surface 410 of the hub 4.

The protector 8 is further configured and to be fixed relative to the sleeve 2 when the hub 4 moves from the injection position to the safety position. The safety device 1 thus comprises first blocking means configured to prevent the protector 8 from moving back in the distal direction when the hub 4 moves from the injection position to the safety position. The first blocking means may preferably be in the form of first snapping means that are configured to make the protector 8 get snapped with the sleeve 2 as soon as the hub 4 reaches the injection position.

The first snapping means may comprise first resilient legs 81 that are provided on the protector 8. The first resilient legs 81 may extend parallel to the longitudinal axis A. They may be located above the longitudinal slots 24 of the sleeve 2 and may be aligned with said longitudinal slots 24.

The free ends of the first resilient legs 81 are engaged in the longitudinal slots 24 of the sleeve 2 when the hub 4 is being moved from the pre-use position to the injection position. The first resilient legs 81 and the longitudinal slots 24 may thus act as guiding means for guiding the translation of the protector 8 relative to the sleeve 2 before the hub 4 reaches the injection position.

The first resilient legs 81 are configured to radially outwardly deform when abutting against the proximal side of the securing ring 20 of the sleeve 2, so as to disengage the longitudinal slots 24 and pass behind said securing ring 20.

The first resilient legs 81 may comprise a proximal deflecting surface 810 that may be slanted and that is intended to abut against the distal side of the securing ring 20 so as to favor the radial deformation of the first resilient legs 81.

The first resilient legs 81 may comprise a distal abutment surface 812 that is configured to abut against the distal side of the securing ring 20 so as to block a distal movement of the protector 8 when the hub 4 is being moved from the injection position to the safety position.

The first resilient may further include a proximal abutment surface 814 configured to abut against, for example, a distal shoulder 108 of the injection device 100, so as to block a proximal movement of the protector 8 when the protector 8 is in the injection position.

The first resilient legs 81 advantageously include a hook-shaped portion 816 that may be located at their free end, said hook-shaped portions 816 extending radially inwardly so as to engage the longitudinal slots 24 of the sleeve 2 before the hub 4 reaches the injection position, and said hook portions 816 disengaging said longitudinal slots 24 in order to be positioned proximally relative to the securing ring 20 when the hub 4 reaches the injection position. A distal side of the hook-shaped portions 816 may define the distal abutment surface 812. A proximal side of the hook-shaped portions 816 may define the deflecting surface 810 and/or the proximal abutment surface 814.

It should be noted that the safety device 1 might be configured to maintain a distance between the proximal end of the hub 4, more specifically the blocking surface 460, and the distal abutment surface 812 of the first resilient legs 81.

The safety device 1 further comprises second blocking means configured to prevent the hub 4 from moving back in the proximal direction after the hub 4 reaches the safety position. The second blocking means may be in the form of second snapping means that are configured to make the hub 4 be snapped with the protector 8 and/or the sleeve 2 as soon as the hub 4 reaches the safety position.

The second snapping means may comprise second resilient legs 82 that are provided on the protector 8. The second resilient legs 82 may extend parallel to the longitudinal axis A. They may be aligned with the proximal slots 48 of the hub 4.

The free ends of second resilient legs 82 are engaged in the proximal slots 48 of the hub 4 when the hub 4 is being moved from the pre-use position to the injection position. The second resilient legs 82 and the proximal slots 48 may thus act as guiding means for guiding the translation of the hub 4 relative to the protector 8 before the hub 4 reaches the safety position.

The second resilient legs 82 are configured to radially outwardly deform when abutting against the proximal side of the blocking ring 46 of the hub 4, so as to disengage the proximal slots 48 and pass behind said blocking ring 46.

The second resilient legs 82 may comprise a proximal deflecting surface 822 that may be slanted and that is intended to abut against the blocking ring 46 so as to favor the radial deformation of the second resilient legs 82.

The second resilient legs 82 may comprise a distal abutment surface 820 that is configured to abut against the distal side of the blocking ring 46 so as to block a proximal movement of the hub 4 once the hub 4 is in the safety position. It should be noted that the distal abutment surface of the second resilient legs 82 advantageously corresponds to the distal abutment surface 820 that is pushed by the pushing surface 410 of the hub 4.

The second resilient legs 82 advantageously include a hook-shaped portion 824 that may be located at their free end, said hook-shaped portions 824 radially inwardly extending in the proximal slots 48 of the hub 4 before the hub 4 reaches the safety position, and disengaging said proximal slots 48 in order to be positioned proximally relative to the blocking ring 46 when the hub 4 reaches the safety position. A distal side of the hook-shaped portions 824 may define the distal abutment surface 820. A proximal side of the hook portions may define the proximal deflecting surface 822.

It is contemplated that the second snapping means may alternatively or complementarily comprise the longitudinal legs 22 of the sleeve 2 that may pass behind the intermediate ring 41 of the hub 4 when the hub 4 reaches the safety position, the blocking surface 224 of the radial protrusion 220 abutting against the proximal side of the intermediate ring 41, thereby preventing the hub 4 from being translated back in the proximal direction when the hub 4 is in the safety position.

The protector 8 advantageously comprises a support ring 80 that surrounds the hub 4 and that both supports the first and the second resilient legs 81, 82. More specifically, the first resilient legs 81 proximally extend from said support ring 80 while the second resilient legs 82 distally extend from said support ring 80. The first resilient legs 81 and the second resilient legs 82 may be offset in a circumferential direction of the support ring 80, thereby alternating along the circumference of the support ring 80. The first and second resilient legs 81, 82 may be regularly distributed along the support ring 80.

Figure 6:
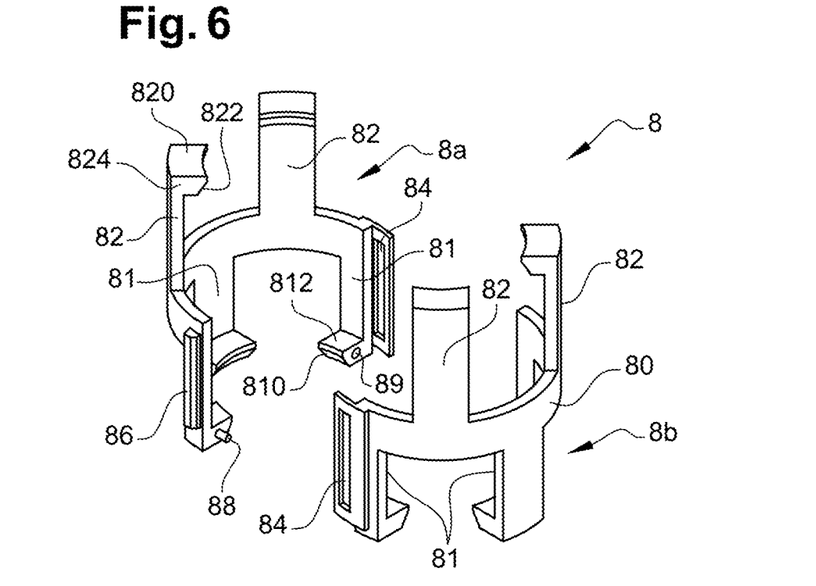
FIG. 6 is a perspective view of a disassembled protector of a safety device according to an embodiment of the invention.

With reference to FIGS. 2 and 6, the protector 8 may be made of two parts 8a, 8b assembled to each other, each of said parts 8a, 8b corresponding to a semi-circular half of said support ring 80. As a result, the two halves of the protector 8 may be assembled directly around the hub 4. The two parts 8a, 8b may be identical. More specifically, the two parts 8a, 8b may comprise snapping means so as to be secured to each other. The snapping means may comprise an axial slot 84 configured to receive an axial rib 86 provided on the other part, and an axial rib 86 configured to engage the axial slot 84 of said other part. The two parts 8a, 8b of the protector 8 may further comprise guiding means, such as a rod 88 configured to enter a hole 89 of the other part and a hole 89 configured to receive a rod 88 of said other part. The guiding means may be orthogonal to the longitudinal axis A and orthogonal to the bond line of said two parts 8a, 8b.

With reference to FIGS. 1 and 2, the invention also relates to an injection device 100, such as a prefilled or prefillable syringe, comprising a barrel 106 defining a reservoir for a medical product, a distal tip 104 defining a passageway in communication with the reservoir and a needle 102 secured to the distal tip 104 so as to allow said medical product to be injected into an injection site. The injection device 100 further comprises a passive safety device 1 as above described, said safety device 1 being secured onto the distal tip 104.

The barrel 106 defines a distal shoulder 108 that delimits with the sleeve 2 a groove intended to receive the first blocking means when the hub 4 reaches the injection position. The distal shoulder 108 may block a proximal movement of the protector 8 relative to the sleeve 2, thereby preventing a proximal movement of the hub 4 relative to the sleeve 2 when the hub 4 is blocked in the safety position by the distal abutment surface 820 of the protector 8.

Figure 7A:
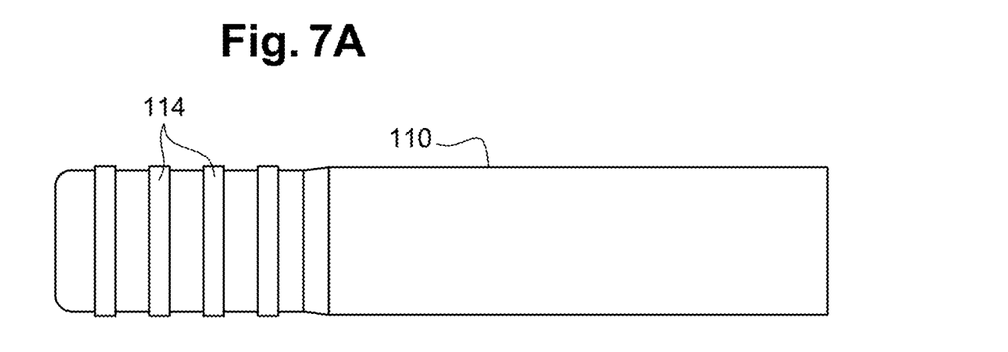
FIG. 7A is a side view of a cap of an injection device according to an embodiment of the invention.
Figure 7B:
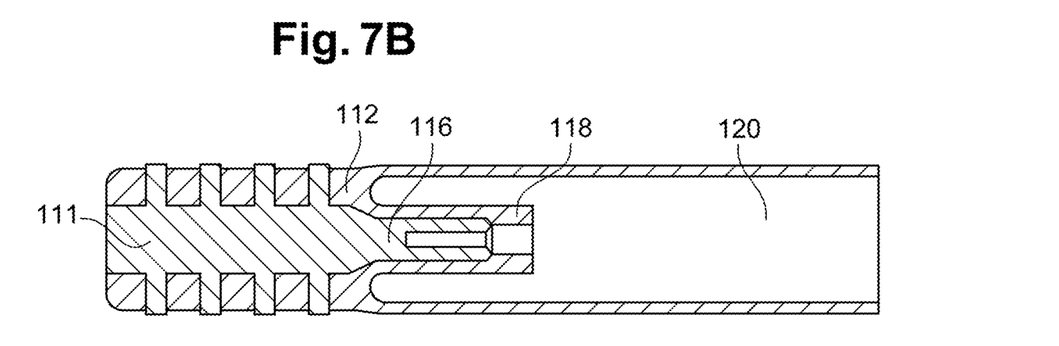
FIG. 7B is a cross-section view of a cap of an injection according to an embodiment of the invention.

With reference to FIGS. 7A and 7B, the injection device 100 may further comprise a cap 110 configured to be mounted onto the safety device 1. The cap 110 may be made of two different materials, for example a first inner material 111 such as rubber or TPE and a second outer material 112 such as polycarbonate. The first material 111 may be soft while the second material 112 may be rigid. The inner material 111 may extend through one or more grooves of the second material 112 so as to provide one or more gripping surfaces 114 on an external lateral wall of the cap 110. The inner material 111 may have a portion 116 pricked by the needle when the cap is mounted on the safety device 1. This portion 116 may be surrounded by an inner protective sleeve 118 that may be made of the second material 112. The cap 110 defines a cavity 120 configured to accommodate the safety device 1. The cap 110 is configured to be removed by simply pulling the cap 110 in the distal direction.

The operation of the safety device 1 and the injection device 100 of the invention is described below with reference to FIGS. 8 to 10 and 11 to 13.

The user may firstly remove the cap 110 by pulling the cap 110 along the longitudinal axis A in the distal direction. The safety device 1 is in the pre-use position as shown on FIGS. 8 and 11.

Figure 11:
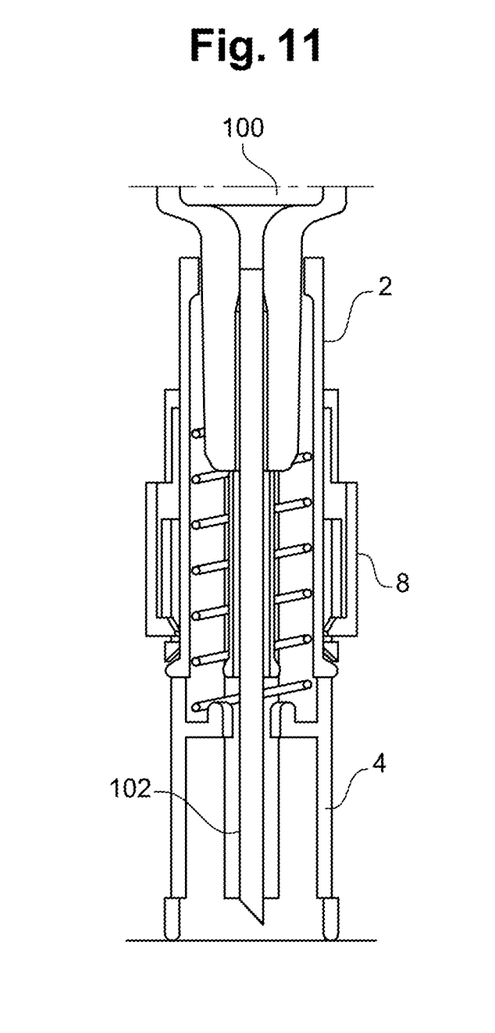
FIG. 11 is a cross-section view of a safety device according to an embodiment of the invention, in the pre-use position.

The user may then apply the distal end of the hub 4 on the injection site and press the injection device 100 against the injection site (FIG. 11). This causes the hub 4 to slide proximally from the pre-use position to the injection position and the needle 102 to enter the injection site. Due to the pushing surface 410 of the hub 4 abutting against the distal abutment surface 820 of the protector 8, the protector 8 slides together with the hub 4 in the proximal direction relative to the sleeve 2. The distal end of the sleeve 2 distally slides in the distal slots 49 of the hub 4. The first resilient legs 81 proximally slide in the longitudinal slots 24 of the sleeve 2. The biasing element 6 is compressed due to the retaining element moving in the proximal direction and thus stores energy.

Figure 9:
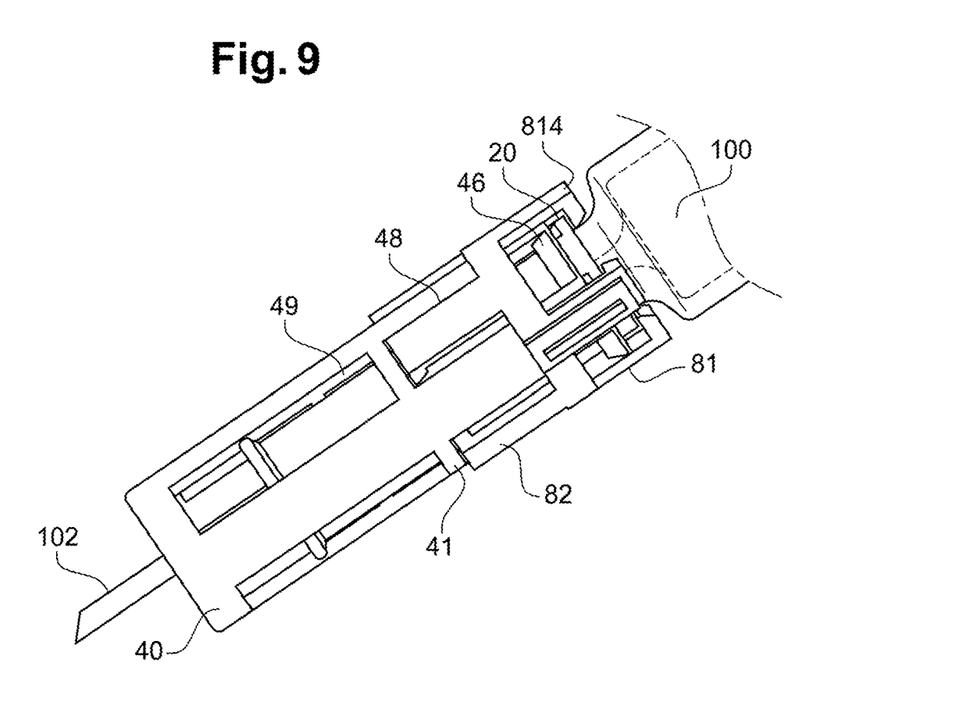
FIG. 9 is a perspective view of a safety device according to an embodiment of the invention, in the injection position.
Figure 10:
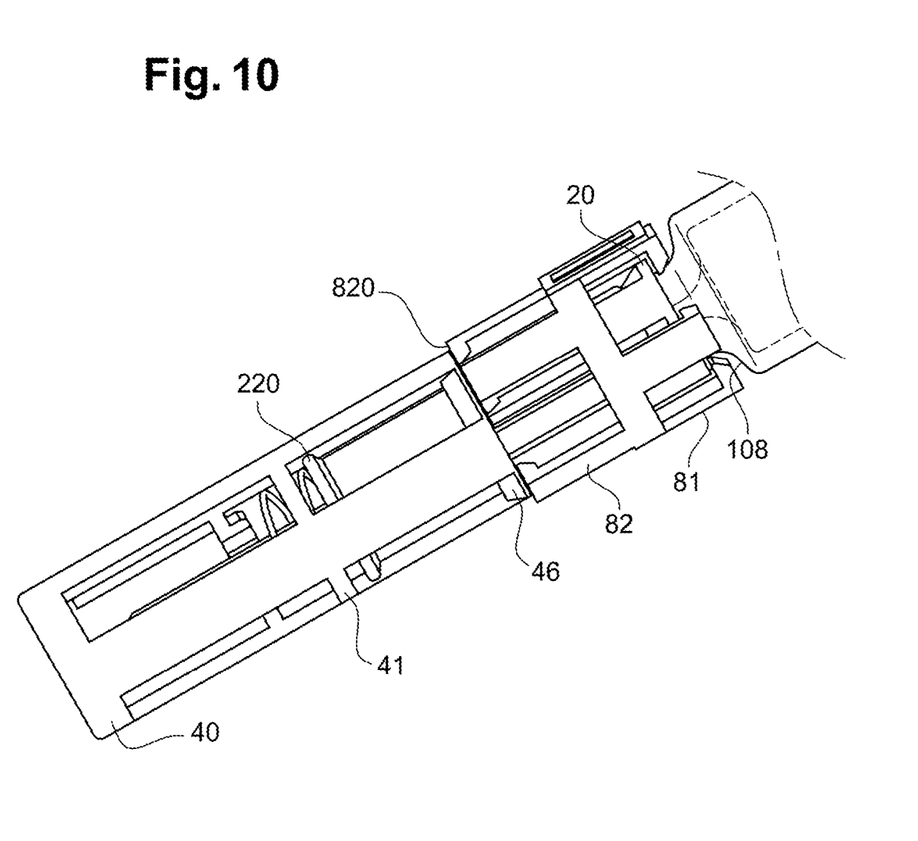
FIG. 10 is a perspective view of a safety device according to an embodiment of the invention, in the safety position.
Figure 12:
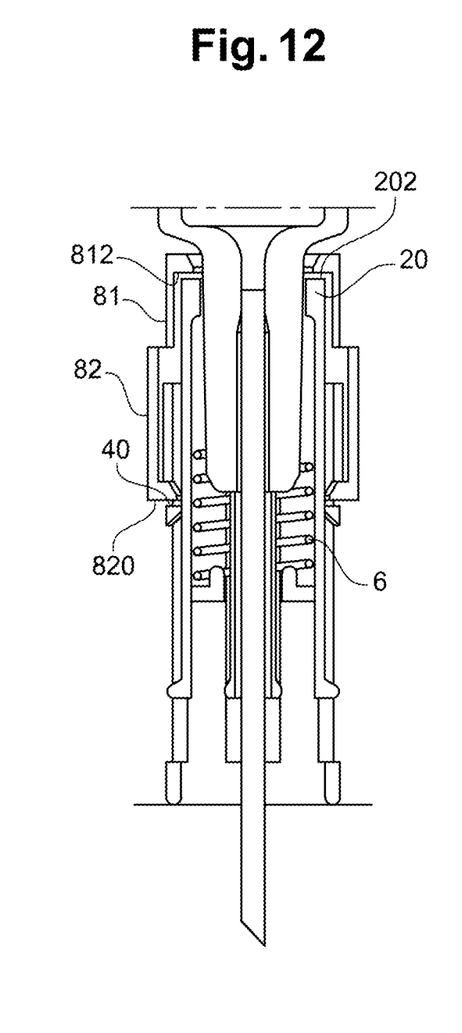
FIG. 12 is a cross-section view of a safety device according to an embodiment of the invention, in the injection position.

When the hub 4 reaches the injection device 100, the free ends of the first resilient legs 81 abut against the distal side of the securing ring 20 and radially deform so as to move behind said securing ring 20. The hook-shaped portion 814 of the first resilient legs 81 is thus blocked between the proximal side of the securing ring 20 and the distal shoulder 108 of the barrel 106, thereby preventing the protector 8 from moving in the distal and proximal directions (FIGS. 9 and 12).

Figure 13:
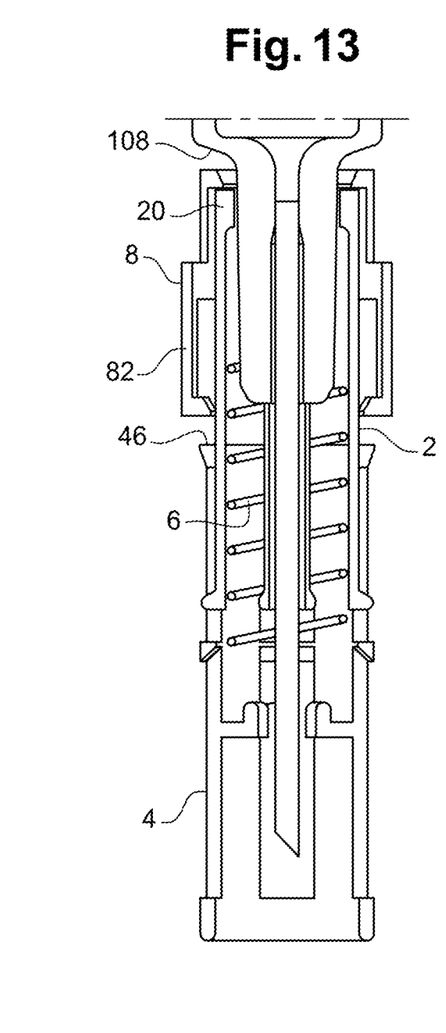
FIG. 13 is a cross-section view of a safety device according to an embodiment of the invention, in the safety position

When the injection is completed, the user withdraws the needle 102 from the injection by pulling the injection device 100 away from the injection site. The biasing element 6 thus releases its stored energy, thereby causing the hub 4 to slide back relative the sleeve 2 from the injection position towards the safety position in the distal direction. The protector 8 however remains in the injection position, due to the abutment of the distal abutment surface 812 of the hook-shaped portion 814 against the abutment surface 202 of the securing ring 20. The second resilient legs 82 accordingly slide into the proximal slots 48 in the proximal direction.

When the hub 4 reaches the safety position, the free ends of the second resilient legs 82 abut against the distal side of the blocking ring 46 of the hub 4 and thus radially deform so as to move behind said blocking ring 46. The free ends of the longitudinal legs 22 of the sleeve 2 may, before or simultaneously, abut against the distal side of the intermediate ring 41 and deform radially inwardly so as to move behind said intermediate ring 41. Due to the abutment of the proximal side of the blocking ring 46 against the distal abutment surface 820 of the free end of the second resilient legs 82 and/or to the abutment of the proximal side of the intermediate ring 41 against the blocking surface 224 of the free ends of the longitudinal legs 22, the hub 4 is prevented from moving back in the proximal direction. The hub 4 in the safety position thus protects the needle 102 and avoids needle stick injuries.

The invention also relates to a method for manufacturing the above-described injection device 100, this method comprising the steps of:
(i) securing the needle onto a distal tip 104 of the injection device 100;
(ii) positioning the biasing element 6 into the sleeve 2;
(iii) positioning the hub 4 onto the sleeve 2 against the action of the biasing element 6;
(iv) positioning the protector 8 onto the hub 4 and the sleeve 2.

The steps (ii) and (iii) may take place simultaneously.

The step (iii) may comprise the pre-loading of the biasing element 6 until the distal end of the leg of the sleeve 2 abuts against the distal side of the intermediate ring 41 of the hub 4.

The step (iv) may comprise the step of assembling the two-part protector 8 directly around the hub 4 and the sleeve 2. By assembling the two-part protector 8 directly around the hub 4 and the sleeve 2 it should be understood that the result of this assembly is the protector 8 being assembled and positioned onto the hub 4 and the sleeve 2 in a ready for use condition. This step may be performed by means of the above-described snapping and/or guiding means of the two halves of the protector 8.

The invention claimed is:

1. A passive safety device comprising:
   a sleeve having a proximal end fixedly attached to a distal tip of a syringe;
   a hub slidably mounted onto the sleeve between a pre-use position, an injection position wherein the hub is proximally located with regard to the pre-use position, and a safety position wherein the hub is distally located with regard to the injection position;
   a biasing element configured to urge the hub distally towards the safety position;
   a protector configured to slide together with the hub relative to the sleeve between the pre-use position and the injection position;
   first blocking means configured to block a distal movement of the protector when the hub is in the injection position so that the protector is prevented from sliding back together with the hub in a distal direction; and
   second blocking means configured to block a proximal movement of the hub when the hub is in the safety position,
   wherein the protector comprises a support ring surrounding at least a portion of an exterior surface of the hub, the first blocking means comprising at least one first resilient leg proximally extending from said support ring and the second blocking means comprising at least one second resilient leg distally extending from said support ring.

2. The device according to claim 1, wherein the first blocking means further comprise first snapping means configured to make the protector be snapped with the sleeve when the hub reaches the injection position.

3. The device according to claim 2, wherein the first snapping means are provided on the protector.

4. The device according to claim 2, wherein the first snapping means comprise said at least one first resilient leg that is slidably engaged in a longitudinal slot of the sleeve when the hub moves from the pre-use position towards the injection position, said at least one first resilient leg being configured to radially deform against a distal side of a blocking member of the sleeve and abut a proximal side of said blocking member when the hub is in the injection position.

5. The device according to claim 1, wherein the second blocking means further comprise second snapping means configured to make the hub be snapped when the hub reaches said safety position.

6. The device according to claim 5, wherein the second snapping means are provided on the protector.

7. The device according to claim 5, wherein the second snapping means comprise said at least one second resilient leg that is slidably engaged in a proximal slot of the hub when the hub moves from the injection position towards the safety position, said at least one second resilient leg being configured to radially deform against a distal side of a blocking member of the hub and abut a proximal side of said blocking member when the hub is in the safety position.

8. The device according to claim 7, wherein the hub comprises a proximal pushing surface that defines a distal end of the proximal slot of the hub, said proximal pushing surface being configured to abut against the at least one second resilient leg in order to cause said protector to slide together with the hub when the hub moves from the pre-use position to the injection position.

9. The device according to claim 1, wherein the hub comprises at least one inner retaining element, the biasing element comprises a distal end abutting against said inner retaining element in order to exert a distal force on the hub, and the sleeve has a longitudinal slot provided with an open distal end in order to allow said at least one retaining element to penetrate and slide into said longitudinal slot when the hub moves towards the injection position.

10. The device according to claim 1, wherein the at least one first resilient leg and the at least one second resilient leg are offset in a circumferential direction of the support ring.

11. The device according to claim 1, wherein the protector is made of two parts configured to be assembled to each other directly on the hub.

12. An injection device comprising the passive safety device according to claim 1.

13. A method for manufacturing the injection device according to claim 12, comprising the steps of:
   (i) securing the needle of the passive needle safety device onto a distal tip of the injection device;
   (ii) positioning the biasing element of the passive needle safety device into the sleeve;
   (iii) positioning the hub of the passive needle safety device onto the sleeve against the action of the biasing element; and
   (iv) positioning the protector of the passive needle safety device onto the hub and the sleeve.

14. The device according to claim 1, wherein the hub surrounds at least a portion of the sleeve.

15. The device according to claim 1, wherein the hub comprises one or more proximal slots on an exterior surface thereof, the one or more proximal slots extending parallel to a longitudinal axis of the hub.

16. The device according to claim 15, wherein the hub comprises one or more distal slots on an exterior surface thereof, the one or more distal slots being longitudinally aligned with the one or more proximal slots.

17. A passive safety device comprising:
   a sleeve having a proximal end configured to be secured to a distal tip of an injection device;
   a hub slidably mounted onto the sleeve between a pre-use position, an injection position wherein the hub is proximally located with regard to the pre-use position, and a safety position wherein the hub is distally located with regard to the injection position;
   a biasing element configured to urge the hub distally towards the safety position;
   a protector configured to slide together with the hub relative to the sleeve between the pre-use position and the injection position;
   first blocking means configured to block a distal movement of the protector when the hub is in the injection position so that the protector is prevented from sliding back together with the hub in a distal direction; and
   second blocking means configured to block a proximal movement of the hub when the hub is in the safety position,
   wherein the protector comprises a support ring, the first blocking means comprising at least one first resilient leg proximally extending from said support ring and the second blocking means comprising at least one second resilient leg distally extending from said support ring,
   wherein the second blocking means further comprise second snapping means configured to make the hub be snapped when the hub reaches said safety position, and wherein the second snapping means comprise at least one longitudinal leg of the sleeve that is slidably engaged in a distal slot of the hub when the hub moves from the injection position towards the safety position, said at least one longitudinal leg being configured to radially deform against a distal side of a retaining member of the hub and to abut against a proximal side of said retaining member when the hub is in the safety position.

\* \* \* \* \*